United States Patent
Rodelet

(10) Patent No.: US 6,849,279 B2
(45) Date of Patent: Feb. 1, 2005

(54) FRACTION EXTRACTED FROM ARCHAEBACTERIA FOR COSMETIC PURPOSES

(75) Inventor: Jean-François Rodelet, Boulogne Billancourt (FR)

(73) Assignee: Caster, Paris (FR)

( * ) Notice: Subject to any disclaimer, the term of this patent is extended or adjusted under 35 U.S.C. 154(b) by 416 days.

(21) Appl. No.: 10/126,048

(22) Filed: Apr. 19, 2002

(65) Prior Publication Data

US 2003/0017973 A1 Jan. 23, 2003

(30) Foreign Application Priority Data

Apr. 19, 2001 (FR) .......... 01 05287

(51) Int. Cl.$^7$ .......... A61K 35/72
(52) U.S. Cl. .......... 424/780
(58) Field of Search .......... 424/780

(56) References Cited

U.S. PATENT DOCUMENTS 5,091,364 A  2/1992  Baumgarten et al. .......... 514/8

FOREIGN PATENT DOCUMENTS

| EP | 0 286 869 | 10/1988 |
| EP | 0 461 662 | 12/1991 |
| FR | 2590273 | 5/1987 |

OTHER PUBLICATIONS

Database Caplus, Database accession no. 1996:441289.

Database Biosis, Database accession no. 1999:323068.

*Primary Examiner*—Jean C. Witz
(74) *Attorney, Agent, or Firm*—Fulbright & Jaworski, L.L.P.

(57) ABSTRACT

The invention relates to a method for the extraction and use of a glycoprotein fraction extracted from an archaebacterium: *Halobacterium halobium*. The product of the invention, when incorporated into a cosmetic preparation, indeed exhibits the characteristic feature of protecting the cells of the skin from the harmful effects of pollution and/or ultraviolet radiation.

9 Claims, No Drawings

FRACTION EXTRACTED FROM ARCHAEBACTERIA FOR COSMETIC PURPOSES

BACKGROUND OF THE INVENTION

The present application claims priority to French Application No. 01/05287 filed Apr. 19, 2001, the entire text of which is specifically incorporated by reference herein without disclaimer.

1. Field of the Invention

The invention relates to a method for the extraction and use of a glycoprotein fraction extracted from an archaebacterium: *Halobacterium halobium*. The product of the invention, when incorporated into a cosmetic preparation, indeed exhibits the characteristic feature of protecting the cells of the skin from the harmful effects of pollution and/or ultraviolet radiation.

2. Description of Related Art

Halobacteria are classified in the kingdom comprising archaebacteria, one of the three main branches of the phylogenetic tree. The other two are the eubacteria (also called prokaryotes) and the eukaryotes.

Archaebacteria have been identified in all the extreme niches at the frontiers of life: temperatures exceeding 100° C., acidity at pH=0 or salt concentrations which may exceed 30%.

Archaebacteria are equipped with atypical cell walls from which a component of the molecule of peptidoglycan, which is conventionally present in bacteria, muramic acid, is absent. Furthermore, while other organisms manufacture the lipids of their membrane by assembling two fatty acid chains with one molecule of glycerol via an ester bond, the lipids of archaebacteria are composed of long chains of isoprenyl alcohol which are attached to glycerol via ether bonds.

Halobacteria are extreme obligate bacteria. They indeed require, for their growth, very high salt concentrations (from 10 to 30%), KCl, $MgCl_2$ and especially NaCl. These organisms have been isolated from natural media (Great Salt Lake in the USA or the Dead Sea in Israel) or artificial media (salterns). To maintain their internal osmotic pressure which should be in equilibrium with the NaCl concentration in the medium, halobacteria accumulate from 3 to 4 M of salt in their cytoplasm in the form of KCl. A suspension of halobacteria in a medium containing an NaCl concentration of 2 M causes complete loss of the stiffness of the bacterial envelope and the bacterium then assumes a round shape. Decreasing the salt concentration below 1 M leads to bacterial lysis.

Colonies of halobacteria are red in colour, their envelopes indeed contain coloured pigments (bacterio-ruberins) which protect them against intense ultraviolet radiation to which they are exposed.

Among halobacteria, *Halobacterium halobium* further possesses an additional outer envelope, the purple membrane, which serves as support for an original photosynthetic mechanism.

The conventional shape of Halobacterium in a salt-rich medium is that of an oblong bacillus 4 to 10 $\mu$m long and 0.7 $\mu$m in diameter. This bacterium possesses from 5 to 8 lophotrichous flagella. *Halobacterium halobium* is incapable of using carbohydrates as carbon and energy source.

The resistance capacity and the characteristic features of these bacteria make them very promising tools for industry. They are already being exploited in sectors as diverse as the agri-foodstuffs, paper, detergent or pharmaceutical industry.

American Patent Application U.S. Pat. No. 5,091,364 refers to the preparation of envelope glycoproteins extracted from cultures of archaebacteria with the aim, after enzymatic degradation of the glycoproteins, of using them to increase the immune defences of the body against infection.

Patent Application FR 2 590 273 also uses fractions derived from archaebacteria but in combination with synthetic sea water in the context of the manufacture of aesthetic products in dermatology.

SUMMARY OF THE INVENTION

The applicant has discovered that the glycoprotein fraction obtained from a bacterial pellet of *Halobacterium halobium* had advantageous cosmetic properties especially for the protection of skin cells against the harmful action of pollution caused by exhaust fumes and/or ultraviolet radiation.

The subject of the invention is therefore the glycoprotein fraction extracted from archaebacteria.

Another subject consists of the cosmetic composition containing this fraction.

Other subjects will emerge on reading the description and the examples which follow.

The product which is the subject of the invention is characterized in that it comprises a glycoprotein fraction extracted from archaebacteria.

The product according to the invention comprises from 25 to 40% of glycoproteins of archaebacteria.

Preferably, the archaebacteria are halobacteria.

The product may be obtained in the following manner: the bacterial mass obtained from the culture of archaebacteria is first freed from its lipid constituents by two successive extractions, the first with a halogenated solvent and the second with a $C_1$–$C_4$ alkanol, and then extracted with distilled water. The extract obtained is then ultrafiltered in order to remove the residual inorganic salts. After evaporation and drying of the filtrate under vacuum, a yellowish white powder is obtained exhibiting a strong positive reaction to ninhydrin.

The method for extracting the product according to the invention is applied to archaebacteria, preferably to halobacteria, and more particularly to *Halobacterium halobium*.

The glycoprotein fraction obtained according to the method of extraction of the invention is characterized in that it comprises from 25 to 40% of glycoprotein extract of archaebacteria per gram of fraction. This fraction was called SURVIUM.

Another subject of the invention is the use of the protein fraction of the invention for the preparation of a cosmetic formulation for protecting the skin against pollution caused by exhaust fumes and/or ultraviolet radiation.

The cosmetic compositions of the present invention are characterized in that they comprise, in a cosmetically acceptable medium, a glycoprotein fraction according to the invention extracted from archaebacteria, preferably from *Halobacterium halobium*.

The cosmetic compositions of the present invention may contain, in addition to the glycoprotein fraction, water and additives customarily used in cosmetics. These additives are, for example, thickening agents, perfumes, preservatives, emulsifiers, vegetable or mineral oils, antiseptic agents, acidifying or alkalinizing agents, vitamins, anti-UV agents, surfactants, solvents, pH-stabilizing agents, silicones and the like.

The compositions in accordance with the invention may be provided in the form of a milk, cream, lotion, serum, mask or gel.

DETAILED DESCRIPTION OF ILLUSTRATIVE EMBODIMENTS

The following examples are intended to illustrate the invention without, however, being of a limiting nature.

EXAMPLE 1

Extraction of the Glycoprotein Fraction Obtained from *Halobacterium halobium*

The bacterial mass cultured according to the protocol published by D. Oesterhelt and W. Stoeckenius and frozen is provided by the Centre National de la Recherche Scientifique in the form of a compact, granular substance having a reddish colour.

A quantity of bacterial mass is dispersed beforehand in a small amount of dichloromethane (nonpolar solvent) with an ultra-thurax apparatus in an amount of 40 grams of bacterial mass per 100 ml of solvent. This dispersion is poured into an extraction cartridge made of cellulose and the whole is placed in the receptacle of the Soxhlet extractor (Macherey-Nagel). The flask is filled with 500 ml of solvent and the closed apparatus is placed in a waterbath thermostatted at 85° C. After 6 hours of extraction, the cartridge drained and dried under vacuum undergoes a second extraction with 99.9% ethanol and at a temperature of 90° C. A final extraction is carried out with distilled water for 6 hours. The solution obtained is then concentrated in a rotary evaporator under vacuum (Rotavapor).

The concentrate obtained contains a high proportion of inorganic salts and should be purified. It is redissolved in a minimum of distilled water and the saline fraction is removed by ultrafiltration using a Macrosep cell (Pall-Filtron), centrifuged at 5000 rpm, which makes it possible to remove the constituents having a molecular mass of less than 1 kD. The purified fraction is then dried in a desiccator under vacuum. The calculated extraction yield is 8% of the initial bacterial mass.

EXAMPLE 2

Evaluation of the Cytotoxicity of the Protein Fraction to be Tested

The viability of the cellular lawns is estimated by an MTT test. The quantification of the metabolic activity of the mitochondrial dehydrogenases is performed by measuring the hydrolysis of MTT. Indeed, the conversion of colourless tetrazolium salt (MTT) to blue formazan crystals is proportional to the activity of a mitochondrial enzyme: succinate dehydrogenase. Thus, the formazan concentration is proportional to the quantity of live cells in the well.

The bacterial product to be tested, obtained from the glycoprotein fraction extracted, is dissolved in solution.

The stock solution is then prepared by dissolving 20% (weight/volume) of the bacterial product in culture medium.

The test is carried out on cultures of human keratinocytes. The cells are cultured in 96-well plates, in the presence of the test product for 24 hours. After these 24 hours of contact, the cells are rinsed and the culture medium is replaced with the medium containing MTT. The cells are then lysed and the formazan crystals are solubilized in acidic isopropanol. The quantity of formazan obtained is quantified by spectrophotometry at the wavelength of 540 nm.

The cell viability (mean of three tests) is calculated according to the formula $$\% \text{ cell viability} = (OD_{cells+product}/OD_{untreated\ cells}) \times 100$$

Cell Viability as a Function of the Quantity of Product to be Tested

| % of the stock solution in the medium | Cell viability in % |
|---|---|
| 0 | 100 |
| 0.00013 | 96 |
| 0.0006 | 109 |
| 0.0032 | 100 |
| 0.016 | 88 |
| 0.08 | 74 |
| 0.4 | 66 |
| 2 | 70 |
| 10 | 85 |

The bacterial product concentration which is selected for the following tests is the last which does not show toxicity towards the cells in culture. Thus, the concentration selected is 0.0032 of the stock solution which corresponds to 6.4 µg/ml of product.

EXAMPLE 3

Determination of the Cytotoxicity of the Pollutant Used

The pollutant consists of exhaust gas residues. The pollutant particles are recovered on filters. The water-soluble components of pollutant are first eluted in culture medium. The fibres are then rinsed with ethanol and then immersed in the medium and the whole is vortexed. After 3 hours at room temperature, the preparation is centrifuged at 1500 rpm for 5 minutes. The volume of supernatant is adjusted to 20 ml. The medium thus obtained is then homogeneous and has a grey colour.

The viability of the cellular lawns is estimated by an MTT test described above.

Viability of the Cells in the Presence of Pollutant at Various Concentrations in the Culture Medium

| Concentration in polluted medium (in %) | Viability of the cells in % |
|---|---|
| 0 | 100 |
| 0.78 | 94 |
| 1.56 | 103 |
| 3.12 | 113 |
| 6.25 | 111 |
| 12.5 | 102 |
| 25 | 99 |
| 50 | 74 |
| 100 | 53 |

In the following experiments, the pollutant will be used either pure or diluted by half.

EXAMPLE 4

Quantification in vitro of the Effect of the Bacterial Product on the Energy Metabolism of Human Keratinocytes in Culture The assay of ATP by the indirect method is based on the measurement, by bioluminescence, of the photons emitted during the reaction between ATP and D-luciferin in the presence of oxygen, magnesium and luciferase which catalyses the following reaction:

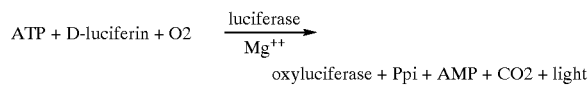

ATP + D-luciferin + O2 $\xrightarrow[Mg^{++}]{luciferase}$ oxyluciferase + Ppi + AMP + CO2 + light The yield of this reaction, corresponding to the ratio of the number of photons emitted to the number of moles of ATP which has reacted, is total.

The cells are cultured in 24-well plates in the presence or in the absence of the product, the pollutant, or the mixture of product+pollutant. The measurements are carried out in triplicate. The cellular lawns are washed in PBS and the cells are lysed on ice with 100 µl of water containing 0.2% Triton X100 (Sigma). The assay of ATP is carried out with an "ATP bioluminescence kit HS II" assay kit (Roche Diagnostics GmbH). The results are obtained from a calibration series.

Effect of the Addition of Product to the Nonpolluted Culture Medium on the Assay of ATP

| Product added to the medium | Quantity of ATP measured (in nmol/ml) | % relative to the negative control |
|---|---|---|
| 0 (control) | 3.152 | 100 |
| Solution containing 6.4 µg/ml of bacterial product | 3.091 | 98 |

The bacterial product to be tested does not have a significant effect on the quantity of ATP synthesized. The inhibition due to the product is negligible.

Effect of the Pollution of the Culture Medium on the Assay of ATP

| Type of medium | Quantity of ATP measured (in nmol/ml) | % relative to the negative control (nonpolluted medium) |
|---|---|---|
| Nonpolluted medium | 3.152 | 100 |
| Polluted medium diluted ½ | 2.373 | 75 |
| Undiluted polluted medium | 1.995 | 63 |

The pollutant which is pure or diluted by half inhibits the synthesis of ATP.

Assay of ATP Synthesized in the Presence of the Bacterial Product and of Polluted Medium The protection index is calculated in the following manner:

P.I.=100−{100×({{nonpolluted medium treated−polluted medium treated}÷{nonpolluted control medium−polluted control medium}}}

| Culture medium | Product added | Quantity of ATP nmol/ml | % of the control | P.I. |
|---|---|---|---|---|
| Nonpolluted medium | Solution containing 6.4 µg/ml of product | 2.206 | 100 | — |
| Polluted medium diluted ½ | | 2.162 | 98 | 92 |
| Undiluted polluted medium | | 2.118 | 96 | 88 |
| Nonpolluted medium | Control free of product | 2.309 | 100 | — |
| Polluted medium diluted ½ | | 1.767 | 77 | — |
| Undiluted polluted medium | | 1.576 | 68 | — |

From these results, the bacterial product tested does not reduce the ATP stock in the nonpolluted medium and protects the cells in culture from the effect of the pollutant (88 and 92% as protection index respectively).

EXAMPLE 5

Determination in vitro of the Anti-free Radical Effect of the Product to be Tested on Suspension of Human Keratinocytes Human keratinocytes are cultured in KGM medium (Keratinocytes Growth Medium) enriched with growth factors and antibiotics. This medium is in fact composed of HEPES buffer at pH 7.4, essential and nonessential amino acids, vitamins and minerals as well as organic compounds and inorganic salts. The growth factors are HKGS (Human Keratinocyte Growth Supplement), BPE (Bovine Pituitary Extract), bovine insulin, hydrocortisone, bovine transferrin and human EGF (Epidermal Growth Factor).

The cells are trypsinized and suspended at $10^6$ cells per milliliter of medium. These keratinocytes are irradiated for 30 minutes with a Helarium lamp emitting ultraviolet A and B radiation in order to activate the synthesis of free radicals. The keratinocyte suspension, containing or otherwise the test product, is acidified at the end of the irradiation (50 µl of citric acid at 2 mol/l per 260 µl of cell suspension in order to obtain a suspension at pH 3.3) and a catalase solution is added. In fact, 100 µl of methanol/tert-butanol and 400 µl of distilled water are added to the cell suspension and then 15 µl of catalase at 0.2 mg/ml per 100 µl of the preceding suspension are added in order to eliminate the hydrogen peroxide which may react and create a false signal.

A luminescent reagent is then added. The peroxides formed, resulting form the action of the free radicals on the cells, are then assayed by chemiluminescence. The reading carried out for one minute by the luminometer totals the number of relative luminescence units (RLU) emitted.

The test product is diluted in the culture medium at a concentration of 6.4 µg/ml and added or otherwise to the suspension of keratinocytes.

The protective power of the product against the synthesis of free radicals is represented by the efficacy E expressed in % and calculated by the formula:

$$E\ \%=(CI-CTI)\div(CI-CNI)\times 100$$

where CI represents the irradiated cells not treated with the product, CTI the cells irradiated and treated with the product and CNI the nonirradiated and untreated cells.

Estimation of the Action of the Bacterial Product on the Synthesis of Free Radicals

|  | Control Non-irradiated cells (CNI) | Control Irradiated cells (CI) | Non-irradiated cells with product (CT) | Irradiated cells with product (CTI) |
|---|---|---|---|---|
| Test 1 | 1211 | 63222 | 7283 | 37678 |
| Test 2 | 1800 | 101000 | 7300 | 17100 |
| Test 3 | 1281 | 104458 | 3444 | 46844 |
| Mean | 1431 | 91227 | 6009 | 33874 |
| SEM | 186 | 11545 | 1283 | 8795 |
| E % |  |  | 64% |  |

Under the conditions of this study, the action of bacterial product to cells exposed to ultraviolet radiation protects them from the formation of free radicals. This product exhibits a 64% anti-free radical protective effect.

EXAMPLE 6

Quantification in vitro of the Antipollution Effect of a Cream Containing the Bacterial Product This involves a randomized comparative study (product against placebo) carried out according to an intra-individual design. The two creams are applied to each volunteer.

The cosmetic creams are prepared according to the following formula:

|  | Cream 5090 in % | Cream 5091 in % |
|---|---|---|
| Vegetable oil | 8.00 | 8.00 |
| Cyclomethicone | 6.70 | 6.70 |
| Self-emulsifiable glycol stearate | 5.80 | 5.80 |
| Mineral oil | 4.00 | 4.00 |
| Cetyl alcohol | 1.00 | 1.00 |
| Preservative | 0.50 | 0.50 |
| Carbomer | 0.40 | 0.40 |
| Triethanolamine | 0.40 | 0.40 |
| Aqueous extract of *Halobacterium halobium* obtained according to the method of Example 1 at 1 mg/g of cream | — | 0.10 |
| Demineralized water | qs 100% | qs 100% |

The antipollution power of a cosmetic or dermo pharmaceutical product is evaluated by calculating the percentage protection of the skin against microparticles of carbon relative to an untreated area (and/or to a placebo). The polluting particles used as atmospheric pollution markers are carbon microparticles in suspension in water.

The protocol for the inclusion of volunteers in this study is defined by the following points:
Female sex
over 18 years old
Caucasian type
Phototype II-III-IV Excluded from this protocol are pregnant or breastfeeding women, women having a skin disease or a desquamation and/or erythema on the experimental area as well as volunteers suffering from a serious or progressive disease. Women on anti-inflammatory, corticoid or retinoid medication are also excluded from this protocol.

This protocol is carried out on ten volunteers who accepted not to use dermopharmaceutical or cosmetic products in the areas to be studied on the day of the study.

Summary Table of the Volunteers Included in the Protocol

| Number | Sex | Average age | Type | Phototype |
|---|---|---|---|---|
| 10 | female | 34 ± 4 years | Caucasian | III |

Two types of cream are tested:
Cream 5090 which is a placebo
Cream 5091 which has a composition identical to that of cream 5090 to which the bacterial product has been added at a final concentration of 1 mg/ml An area of 16 $cm^2$ is defined on each forearm (a placebo area and a treated area). At t=0, the placebo and the test product are applied to the two areas defined in a standardized quantity (2 $\mu l/cm^2$), that is to say that 32 $\mu l$ of cream 5090 and 5091 are applied to each area according to the area, and then the relevant area is lightly massaged with a circular movement using a fingerstall for 15 seconds. At t=20 min, the pollutant is applied to each area defined in a standardized quantity (2 $\mu l/cm^2$). At t=60 min, after standardized rinsing and drying of the areas studied, image acquisition of each area is taken (three images taken per area). The visualization of the pollutant particles at the surface of the skin is carried out using a videomicroscope equipped with a mobile and fibre optic, ×100 length coupled to a computer system for image acquisition.

To express the reduction in "pollution" observed on the skin of the area treated with the product or the placebo, the results are given as percentage protection (P %) according to the following formula:

P %={(ZAV−ZAP)÷ZAV}×100 where ZAV is the quantity of carbon particles measured (in pixels) on the area before rinsing and ZAP the quantity of carbon particles which is measured (in pixels) after rinsing. SEM represents the standard error of the mean of the results for the ten volunteers.

Si P %=100%; then the protection against pollution is total, the surface of the skin no longer exhibits any trace of carbon particles.

Amount of Polluting Particles on the Areas Studied Before and After Rinsing

|  | Cream 5090 (placebo) | | Cream 5091 (5090 + bacterial product at 1 mg/ml) | |
|---|---|---|---|---|
|  | before rinsing (ZAV) | after rinsing (ZAP) | before rinsing (ZAV) | after rinsing (ZAP) |
| Mean for the volunteers | 71327 | 31725 | 65196 | 14792 |
| SEM | 6706 | 4557 | 5508 | 2796 |
| P % | 56 | | 77 | |

Under the conditions of this study, a difference is noted between the results obtained with the placebo and those obtained with the cream containing the product to be tested. The placebo protects the skin by 56% whereas the cream containing the bacterial extract protects the skin by 77%.

EXAMPLE 7

Types of Cosmetic Formulation

| Formulation of moisturizing protective lotion | |
|---|---|
| Demineralized water | qs 100 ml |
| Glycerin | 5.00 |
| PEG-40 hydrogenated castor oil | 3.00 |
| Panthenol | 0.30 |
| Chlorhexidine | 0.20 |
| *Halobacterium halobium* extract according to the invention | 0.02 |
| Perfume | qs |

| Antisun milk formulation | |
|---|---|
| Demineralized water | qs 100 ml |
| Mineral oil | 7.00 |
| Glycerol stearase S.E. | 6.20 |
| Isopropyl myristate | 5.50 |
| Ethylhexyl methoxycinnamate | 4.00 |
| Butyl methoxydibenzoylmethane | 2.00 |
| Cetyl alcohol | 0.30 |
| Carbomer | 0.30 |
| Triethanolamine | 0.25 |
| *Halobacterium halobium* extract according to the invention | 0.10 |
| Imidazolidinyl urea | 0.20 |
| Methylparaben | 0.05 |
| Propylparaben | 0.05 |
| Perfume | qs |

| Make-up gel base formulation | |
|---|---|
| Demineralized water | qs 100 ml |
| PEG-7 glyceryl cocoate | 4.50 |
| Sorbitol | 3.00 |
| Propylene glycol | 2.50 |
| Carbomer | 0.60 |
| Triethanolamine | 0.60 |
| Polyvinylpyrrolidone | 0.50 |
| *Halobacterium halobium* extract according to the invention | 0.10 |
| Imidazolidinyl urea | 0.40 |
| Perfume | qs |

| Make-up cosmetic cream base formulation | |
|---|---|
| Demineralized water | qs 100 ml |
| Cetearyl glucoside | 6.30 |
| Cyclomethicone | 7.00 |
| Isostearyl isostearate | 6.00 |
| Cetearyl alcohol | 3.00 |
| Cetyl alcohol | 1.50 |
| Butyrospermum Parkii (shea butter) fruit | 2.00 |
| PVP/dimethylaminoethyl methacrylate copolymer | 0.50 |
| Dimethicone | 0.50 |
| Xanthan gum | 0.30 |
| *Halobacterium halobium* extract according to the invention | 0.05 |
| Imidazolidinyl urea | 0.20 |
| Perfume | qs |

What is claimed is:

1. A cosmetic composition comprising an archaebacteria glycoprotein fraction in an amount by weight of 25% to 40% in a cosmetically acceptable medium.

2. The cosmetic composition of claim 1, wherein the archaebacteria glycoprotein fraction is further defined as a halobacteria glycoprotein fraction.

3. The cosmetic composition of claim 1, further defined as a gel, a milk, a lotion, a serum, a mask, or a cream.

4. A method of producing an archaebacteria glycoprotein fraction comprising:

obtaining a bacterial mass by culturing archaebacteria;

extracting the bacterial mass with three successive extractions, the extractions comprising:

(a) a halogenated solvent;

(b) a $C_1$–$C_4$ alkanol; and (c) water, wherein an archaebacteria glycoprotein fraction is obtained.

5. A method for protecting skin cells comprising:

obtaining a cosmetic composition comprising an archaebacteria glycoprotein fraction in an amount by weight of 25% to 40% in a cosmetically acceptable medium; and applying the cosmetic composition to the skin.

6. The method of claim 5, further defined as a method of protecting skin cells from pollution caused by exhaust gases and/or ultraviolet radiation.

7. The cosmetic composition of claim 2, wherein the halobacteria glycoprotein fraction is further defined as a *Halobacterium halobium* glycoprotein fraction.

8. The method of claim 4, wherein the archaebacteria glycoprotein fraction is further defined as a halobacteria glycoprotein fraction.

9. The method of claim 8, where the halobacteria glycoprotein fraction is further defined as a *Halobacterium halobium* glycoprotein fraction.

* * * * *